United States Patent [19]
Hills

[11] Patent Number: 6,133,249
[45] Date of Patent: Oct. 17, 2000

[54] PHOSPHOLIPID AND PROPYLENE GLYCOL BASED LUBRICANT

[75] Inventor: Brian Andrew Hills, Cleveland, Australia

[73] Assignee: MacNaught Medical Pty Limited, Turrella, Australia

[21] Appl. No.: 09/077,324

[22] PCT Filed: Dec. 19, 1996

[86] PCT No.: PCT/AU96/00818

§ 371 Date: Nov. 4, 1998

§ 102(e) Date: Nov. 4, 1998

[87] PCT Pub. No.: WO97/22345

PCT Pub. Date: Jun. 26, 1997

[30] Foreign Application Priority Data

Dec. 19, 1995 [AU] Australia ................. 7233/95

[51] Int. Cl.$^7$ ............ A01N 57/26; A01N 57/10; A01N 25/00
[52] U.S. Cl. ............. 514/78; 514/148; 514/938; 514/941; 514/943; 514/773
[58] Field of Search ............. 514/78, 148, 773, 514/941, 943

[56] References Cited

U.S. PATENT DOCUMENTS 4,766,015  8/1988  Nikoloff et al. ............. 427/326

*Primary Examiner*—Theodore J. Criaries
*Attorney, Agent, or Firm*—Sughrue, Mion, Zinn, Macpeak & Seas, PLLC

[57] ABSTRACT

A method of lubrication of a mammalian joint or other physiological articulation which comprises administering a composition comprising one or more phospholipids in association with propylene glycol.

18 Claims, 1 Drawing Sheet

PHOSPHOLIPID AND PROPYLENE GLYCOL BASED LUBRICANT

This application is a rule 371 of PCT/AU 96/00818 filed Dec. 19, 1996.

FIELD OF THE INVENTION

The present invention relates to methods of lubrication, and in particular, but not exclusively, to methods of lubrication of mammalian joints and other mammalian physiological articulations.

BACKGROUND OF THE INVENTION

It is known that in mammals in general and particularly in man, synovial fluid acts to effectively lubricate the surfaces of bones that are in frictional contact to form joints, as well as lubricating other physiological articulations such as muscles, tendons, ligaments, cartilage or bones which move relative to other muscles, ligaments, tendons, cartilage or bones. For example, the synovial fluid is able to provide effective lubrication in joints such as the human knee, where the standing applied load is about 3 kg/cm$^2$.

As will be recognised, man and other mammals are susceptible to the widespread and debilitating effects of osteoarthritis and other rheumatic diseases. Osteoarthritis is considered to be a disorder characterised by "wear and tear" of a joint which has often been mechanically abused. It is inherent in osteoarthritis that the lubrication system of the joint is compromised which results in degeneration of the joint such that it then becomes painful to move, especially under load. In many instances, if the patient restricts or stops using that joint as a result of the inherent pain, the disease process is exacerbated due to the further reduction in joint lubrication by synovial fluids. Other disorders are also characterised by reduced lubrication of joints or other physiological articulations such as situations where muscle, ligament, tendon, cartilage or bone moves relative to other muscle, ligament, tendon, cartilage or bone. Such disorders are often associated with over use or injuries, particularly sporting injuries. It is therefore desirable to develop a lubricant composition and method of utilising such a composition to improve the lubrication of joints and other physiological articulations in order to keep the joint or articulation mobile and reduce mechanical stress which often results in pain especially during movement.

It is desirable that such a lubricant and methods of lubrication would reduce the co-efficient of friction between movable surfaces in order to facilitate release of surfaces and initiate motion, reduce wear of articular surfaces as well as, in the case of bone/cartilage, rendering the surfaces hydrophobic and therefore less permeable to fluid to prevent hydration of cartilage (it is commonly found that there is increased hydration of articular cartilage in arthritis).

International Patent Application No. PCT/AU88/00322 advocates the use of a lubricant which comprises a phospholipid in combination with hyaluronic acid and optionally further pharmaceutically acceptable excipients and/or additives. It is noted however, that problems are associated with this prior art composition and its method of use as a joint lubricant. Some of these problems are (a) that hyaluronic acid is extracted and purified from birds, animals and other living organisms and for this reason it can include impurities which may result in an immunogenic or pyrogenic response; (b) hyaluronic acid per se initiates an appreciable inflammatory reaction in animal tissues; (c) there are limits to the capability of hyaluronic acid to carry phospholipids in reversible chemical association such that in order to introduce sufficient phospholipid levels into an animal joint or articulation in order to improve lubrication under load, it is necessary to administer a relatively large dose of the phospholipid/hyaluronic acid composition.

International Patent Publication No. PCT/AU91/00063 by the same applicants as the present application proposed an artificial tear composition comprising a phospholipid and optionally hyaluronic acid or a physiologically suitable salt thereof, in an opthalmically suitable carrier. It was disclosed that one possible carrier was propylene glycol. It was not considered at the time, however, that such a composition could be utilised for lubrication of animal joints or other physiological articulations (as defined herein).

It was also considered that the composition referred to in PCT/AU91/00063 would not be appropriate for lubrication of animal joints due to the fact that phospholipid would not be suitably miscible with propylene glycol. Further, it would be anticipated that as phospholipid is highly insoluble in water, that when a solution of phospholipid and a solvent is diluted with water the phospholipid would precipitate in granular form and would be ineffective as a lubricant. Unexpectedly however, it has been found that propylene glycol is totally miscible with phospholipids, such as Dipalmitoyl phosphatidylcholine (DPPC), at all concentrations, so that it is possible to prepare solutions of phospholipid in propylene glycol of concentrations up to 1 g phospholipid per ml of propylene glycol. This compares most favourably with the maximum concentration of phospholipid/hyaluronic acid mixtures of 200 mg phospholipid per 1 ml hyaluronic acid. It was also unexpectedly found that when administered within a joint, and thereby in contact with aqueous synovial fluid, there was no evidence of floccular precipitation and the articular surfaces became exceptionally slippery.

In addition it has been found that when propylene glycol is administered in association with phospholipid that the phospholipid ameliorates any minor inflammatory response which may result from the propylene glycol such that there is overall either no or only a minor and insignificant inflammatory response elicited.

Furthermore, mixtures of phospholipid and propylene glycol are heat stable so that they can be autoclaved to effect sterilisation. It is also noted that propylene glycol is manufactured synthetically and thereby substantially eliminates the possibility of immunogenic or pyrogenic materials being included within a composition administered to an animal.

Accordingly, it is an object of the present invention to provide methods of lubrication of mammalian joints and other physiological articulations (as defined herein). It is a further object of the present invention to at least substantially overcome the problems associated with the prior art lubrication methods, as mentioned herein. Other objects of this invention will become apparent from the following description thereof.

SUMMARY OF THE INVENTION

According to one embodiment of the present invention there is provided a method of lubricating a mammalian joint or other physiological articulation which comprises administering to a joint or articulation in need of such treatment an effective amount of a composition comprising one or more phospholipids, in association with propylene glycol.

In accordance with another embodiment of the present invention there is provided an agent for use in a method of lubricating a mammalian joint or other physiological articulation, which agent comprises an effective amount of one or more phospholipids, in association with propylene glycol.

The present invention also relates to the use of a pharmaceutical composition comprising one or more phospholipids in association with propylene glycol in a method of lubricating a mammalian joint or other physiological articulation.

According to a further embodiment of the present invention there is provided a method of manufacture of a pharmaceutical composition for use in a method of lubricating a mammalian joint or other physiological articulation which comprises admixing one or more phospholipids with propylene glycol.

DETAILED DESCRIPTION OF THE INVENTION

Figure 1:
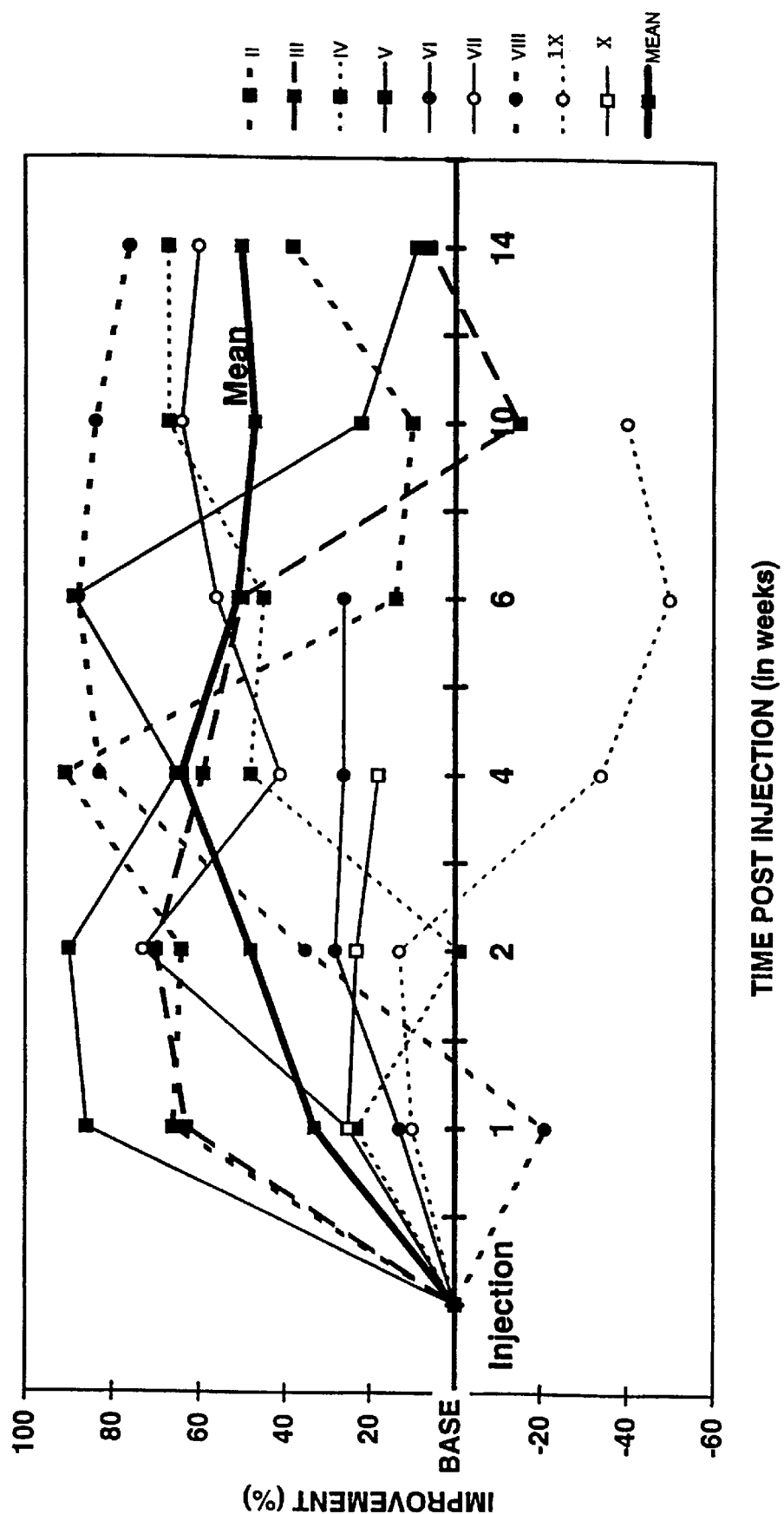
FIG. 1 shows percentage improvement over time post treatment for each of patients I to X undergoing a pilot clinical study in human patients suffering from osteoartliritis of the knee. Patients have been administered 400 mg DPPC in 2 ml. PG by intra-articular injection in the symptomatic knee. Percentage improvement is based upon average WOMAC and LEQUESNE index scores.

Throughout this specification, unless the context requires otherwise, the word "Comprise", or variations such as "comprises" or "comprising", will be understood to imply the inclusion of a stated element or integer or group of elements or integers but not the exclusion of any other elements or integer or group of elements or integers.

Throughout this specification the term "joint" is intended to indicate the point at which two or more bones are connected. Generally the opposing surfaces of bone are lined with cartilaginous or fibrous tissue. The types of joints which the method of the present invention relates to include freely movable (*diarthrosis*) joints, slightly movable (*amphiarthrosis*) joints and immovable (*synarthrosis*) joints. In particular, the present application relates to freely movable and slightly movable joints.

Also considered to be within the scope of the term "joints" are artificial or prosthetic joints which may have been implanted into a mammal. Such joints may have been manufactured from stainless steel or other metallic alloys, ceramics, plastics or other suitable materials. It is possible for the joints which the method of the present invention is intended to treat to comprise a wholly artificial implanted joint or in fact merely a partially implanted joint, such as for example the case where a synthetic ball on the head of the femur bone is implanted into a mammal to articulate with the cartilage lined bony socket of the pelvis.

The methods according to the present invention are particularly suited to the lubrication of artificial joints as well as to lubrication of joints or other physiological articulations during or after surgical intervention. The reason for this is that lubrication using the methods of the present invention helps to prevent surgical adhesions which can be a complication of implantation of prosthetic joints or other surgical procedures.

Throughout the present specification the term "other physiological articulations" is intended to include articulations other than the joints defined above such as for example the situations within a mammalian body where muscle, ligament, tendon, cartilage or bone moves relative to other muscle, ligament, tendon, cartilage or bone. Examples of such situations are where a ligament or tendon moves across a surface or within a groove of a bone such as ligaments in the human ankle which pass about the lateral malleolus. This specific possibility is mentioned by way of example only and is not intended to be limiting upon the scope of the invention.

As described in the preamble to the present specification lubrication to joints or other physiological articulations is often required in the case of arthritic disorders or other disorders which result in reduced lubrication of joints or other physiological articulations, which may for example result from injury or over use. It is intended that by providing lubrication directly to the joint or other physiological articulation that the co-efficient of friction within the joint or articulation will be reduced to thereby release surfaces and/or facilitate the initiation of motion and/or reduce the wear on articular surfaces and hopefully also reduce the levels of pain which may be experienced in relation to joints or other physiological articulations which require lubrication.

It is envisaged that the mammals which may be treated according to the methods of the present invention include humans, primates (gorillas, chimpanzees, baboons, etc.), farm animals (horses, cattle, sheep, goats, donkeys, pigs, etc.), laboratory animals (mice, rats, rabbits, guinea pigs, etc.), captive wild animals (tigers, elephants, kangaroos, etc.) or domestic animals (cats and dogs). Most preferably however, the methods according to the invention will be utilised to treat humans.

The propylene glycol which is utilised in the methods of the invention has the role of a solvent used as a vehicle for delivery of the lipophilic phospholipids. Propylene glycol, which can be easily synthesised and is readily commercially available, has been approved by the Food and Drug Administration in the United States of America as a vehicle for oral, intravenous and enteral or muscular delivery of drugs and other agents. Although, as indicated above it is known that propylene glycol elicits an inflammatory response in mammalian joints and other physiological articulations, this inflammatory reaction is somewhat less severe relative to the inflammatory reaction elicited by hyaluronic acid. Notably, it has been surprisingly found that when administered in conjunction with the phospholipids according to the invention there is only a minor and substantially insignificant inflammatory reaction evident.

The most advantageous aspect of the use of propylene glycol in the present invention as a vehicle for delivery of phospholipid is that it is completely miscible with phoispholipid, apparently in any proportion of the two compounds. This is most advantageous as relative to prior art lubrication compositions as referred to previously, it is possible when utilising propylene glycol as the delivery vehicle to reduce the overall amount of composition delivered while at the same time introducing a high concentration of phospholipid into the joint or other physiological articulation concerned. It is noted that the phospholipid/propylene glycol mixture changes its character from a mobile solution at a concentration of 100 mg phospholipid/ml propylene glycol to a paste or gel at room temperature at 500 mg phospholipids/ml propylene glycol. Upon heating a 200 mg phospholipid/ml propylene glycol mixture to 37° C. the paste or gel is transformed again to a mobile solution.

While in most applications it will be preferable to utilise a concentration of phospholipid/propylene glycol which is liquid at body temperature, there will be applications where it is preferable to utilise a higher concentration phospholipid/propylene glycol mixture which is in the form of a paste or gel. In particular such higher concentration mixtures may be useful for administration during surgical intervention within a joint or other physiological articulation or for example during the process of implanting a replacement joint or part thereof. Similarly, it has been found that the composition according to the present invention is particularly useful for the lubrication of stainless steel surgical equipment such as for example surgical cutting blades or other devices.

The use of the lubrication compositions of the present invention on surgical equipment and especially on cutting blades such as scalpels or bone saws is particularly advantageous. Presently silicone oils are generally used which are relatively mediocre in ability to reduce friction, and are also unable to be broken down by endogenous enzymes and are potentially toxic. There therefore exists a need for a biologically compatible surgical lubricant.

Not only are lubricants required in surgery to reduce wear and tear on equipment, but more importantly to reduce heat generation. For example, when cutting bone with bone saws sufficient heat may be generated to damage or kill surrounding cells e.g. bone osteocytes. If the bone cutting operation was conducted in order to remove an articular surface so that a prosthetic joint (or part thereof) can be implanted, the heat damage to osteocytes could ultimately compromise the mechanical base of the implant to thereby result in its failure. By utilising the compositions of the invention, friction and therefore heat generation are markedly reduced.

The term "phospholipid" as used throughout the specification indicates any phospholipid selected from the groups of sphingolipids or phosphoglyceride. Preferably, the phospholipid or phospholipids utilised in the present invention are chosen from the group comprising phosphatidylcholine, phosphatidylethanolamine, phosphatidylserine, phosphatidylglycerol, phosphatidylinositol, sphingomyelin and derivatives thereof which are suitable for use in lubricant compositions. In particularly preferred embodiments of the invention the phospholipid is alpha-dipalmitoyl phosphatidylcholine (alpha-DPPC) most preferably, the phospholipid is either racemic or D-enantiomeric alpha-DPPC. The reason for this is that phospholipases endogenous within mammalian system are capable of metabolising the L-enantiomeric form but cannot break down the D-enantiomeric form of alpha-DPPC. It is therefore the case that the D-optical isomeric form will have a longer half life in mammalian systems for lubrication of joints and/or other physiological articulations.

While it is possible for the phospholipids according to the invention to be isolated from natural sources, it is most preferable that the phospholipids should be artificially synthesised in order to reduce the likelihood of introducing unwanted immunogenic or pyrogenic materials into the therapeutic composition.

In preferred forms of the invention the lubricant compositions of the invention will have coefficients of kinetic friction in the order of 0.003 to 0.008 at loads as high as 13 kg/cm$^2$ (such loads would be likely to be experienced in the human knee during periods of intense physical exercise).

The administration of the compositions according to the invention will generally involve administration by injection of the phospholipid/propylene glycol mixture into a joint or other physiological articulation requiring such treatment. However, as mentioned above it is possible for other administration routes to be utilised, such as administration of the composition during surgical intervention. The composition may even be applied in combination with vehicles enabling dermal absorption. It is envisaged that the compositions according to the invention will be within the concentration range of between about 25 mg phospholipid/1 ml propylene glycol to about 1 g phospholipid/1 ml propylene glycol. Preferably however, the concentration range will be between about 25 mg phospholipid/1 ml propylene glycol to about 500 mg phospholipids/1 ml propylene glycol and even more preferably the concentration range will be between about 50 mg phospholipid/1 ml propylene glycol to about 300 mg phospholipid/1 ml propylene glycol. Most preferably however, the concentration will be in the order of about 200 mg phospholipid/1 ml propylene glycol.

It is envisaged that the injectate quanity for administration will be in the order of between about 0.1 ml to about 10 ml, preferably about 0.5 ml to about 5 ml and most preferably about 2 ml. However, it is to be recognised that the injectate quantity or volume will depend upon a number of factors such as the species of mammal being treated, the nature of the disorder, the height and weight of the animal, the sex of the animal, as well as other factors which would be apparent to a skilled physician or veterinarian.

In preferred embodiments of the invention administration of the lubricant composition to a joint or other physiological articulation of a mammal will be repeated periodically. It may be in extreme cases that administration of the lubricant composition will take place daily for a period of time. Or preferably, administration may take place weekly, bi-weekly, monthly, bi-monthly, six-monthly or even annually. These treatment regimes are however mentioned by way of example only, and it is to be recognised that the administration may be carried out simply on a one off basis or indeed with periodical readministration at whatever rate is required. It may in fact be the case that there is no pattern in the duration between various administrations and that administration is simply provided on an as needs basis.

An additional advantage of the present invention is that the mixture of phospholipid with propylene glycol is stable at high temperatures, and for this reason it is possible to autoclave the composition for sterilization purposes. A standard autoclaving regime which is suitable, is for example to autoclave at a temperature of 120° C. for a period of around 20 minutes.

The present invention will now be further described with reference to the following non-limiting examples.

EXAMPLES

Example 1

Animal Trials

For use in animal trials the following phospholipids/propylene glycol mixture was used (unless indicated otherwise): a mixture comprising 100 mg DPPC in 1 ml propylene glycol which was in the form of a solution of injectable viscosity when warmed to body temperature.

Methods

1. Injection of 2 mls of the test solution into the left stifle joint of 4 sheep produced no overt reaction with no guarding of that limb when these animals were observed over 72 hours.

2. In two sheep sacrificed after 72 hours the articular surfaces appeared exceptionally slippery and there was no trace of any precipitation of DPPC and no visual sign of inflammatory reaction.

3. It was then decided to test the product in the radiocarpal joint of horses since these are generally regarded by veterinarians as exquisitely sensitive to any injectate. Two horses were sacrificed 24 hours after injection of 1 ml of the product and the cartilage and synovial fluid were examined. There was no trace of separation of DPPC from solution and no overt signs of any inflammatory reaction. When slithers of cartilage were excised from the articular surfaces, they were so slippery as to be almost impossible to pick up by forceps. In the contraleteral joint, by comparison, such slithers were appreciably easier to pick up by forceps and the adjacent layer of gelatinous fluid was not as thick. These tests, although somewhat qualitative, convinced the inventors that irrigation of the joint had improved lubrication and increased the quantity of lubricant available.

4. More quantitative tests were undertaken in a further 4 horses administered radio-labelled 50 mg DPPC in 1 ml. The solution was injected into one contraleteral joint and the horse was sacrificed 2–10 days later when the cartilage was excised and synovial fluid collected for radio-assay. This provided 4 results which gave half-lives for DPPC retention ranging from 5 days to 18 days. While these half-lives may seem short, the system (when lubricated) breaks down only when the last monolayer is lost. As we are adding at least two orders of magnitude more DPPC to the joint than is normally present, it appears quite likely that the joint would remain lubricated for about one month after an injection.

5. Having established the extreme lubricity imparted by exogenous DPPC and the fact that it is likely to remain in the joint for long enough to be worthwhile clinically, the next step was to look for any inflammatory reaction. Six horses were used in the preliminary trials with doses ranging from 1000 mg DPPC in 5 ml.PG to 100 mg DPPC in 2 ml of a solvent comprising 60%PG+40% EtOH to avoid the gelling which otherwise occurs at room temperature—even though this is readily reversed by warming to 37° C.

The following parameters were used as indices of inflammatory reaction:

1. Protein
2. Alkaline phosphatase (ALP)
3. Leucocyte count
4. Specific gravity

All runs showed some degree of inflammatory reaction which, when samples were taken pre-injection and daily thereafter, showed a peak at 24 hours. The reaction was higher using the solvent (60%PG+40% EtOH) than PG alone and increased with size of dose; 1000 mg DPPC in 5 mlPG was clearly worse than 100 mg DPPC in 2 mlPG.

6. In the next series of trials, the joints of 6 horses were injected with 1 ml of PG only to see whether the solvent was the major cause of the inflammatory reaction. This proved to be the case and so the quantity of solvent was halved, i.e. the product evolved as 100 mg DPPC in 1 ml PG, with a resulting decrease in tie inflammatory reaction shown with 2 more horses.

7. The main series of trials was then devised to compare the inflammatory reaction of the radiocarpal joint to the product (100 mg DPPC in 1 mlPG) with the reactions to other agents commonly injected into that joint in the normal course of clinical practice.

The agents selected for comparison were

1. A standard clinical (1 ml) dose of prilocaine—a local anaesthetic.
2. A standard clinical dose of hyaluromic acid (Hyartil)™ (1 ml) a joint lubricant.
3. PG alone (1 ml)

Results

The following conclusions were reached from the results:

1. The inflammatory reaction of the product is not much greater than PG alone, confirming the results of #6 above and supporting the decision to keep the volume of solvent to a minimum.
2. The product produces less inflammatory reaction than the clinical dose of prilocaine.
3. The reaction to the product is certainly no worse than that displayed by hyaluromic acid (Hyartil)™—an agent used clinically to lubricate the equine joint.

It was concluded that, although there is some inflammatory reaction to tire product, this is minimal and no worse than those of other agents commonly injected into the equine joint.

Conclusions

The above studies lead to the following conclusions:

1. The inventive composition is a remarkable lubricant in vitro, reducing friction to phenomenally low levels under high (physiological) load and at low (physiological) sliding velocities.
2. It retains those properties after injection into the joint.
3. Lubrication properties also include good release and reduction of wear—at least, as recorded in vitro.
4. The active ingredient (DPPC) is retained in the joint for long enough to enable lubrication to be maintained by monthly or fortnightly irrigation.
5. The inflammatory reaction peaks at about 24 hours at a level which would seem well tolerated by comparison with other agents used clinically.

Example 2

Pilot Clinical Study in Human Patients Suffering from Osteoarthritis of the knee.

Aim

To investigate the efficacy and tolerance of one intra-articular injection of Dipalmitoyl Phosphatidylcholine (DPPC) in up to 10 patients with symptomatic osteoarthritis of the knee.

Indication

Symptomatic (painful) osteoarthritis of the knee.

Study Design

Up to 10 patients received 2 mls Dipalmitoyl phosphatidyl choline (400 mg DPPC in 2 ml.PG) by intra-articular injection in the symptomatic knee. Each patient was screened at baseline (one week prior to injection) and then weekly for 2 weeks after injection, then 2 weekly for 4 weeks, then monthly for 3 months. (That is, screening prior to injection and at 1, 2, 4, 6, 10 and 14 weeks post injection).

Study Population

Male or female

Outpatients aged between 40–75 inclusive. Patients with painful idiopathic mild—moderate osteoarthritis of the knee confirmed radiologically and who are willing to discontinue current treatment for the study period may be included.

Paracetamol consumption was allowed for analgesia and was monitored.

Evaluation

The WOMAC Osteoarthritis indexes of pain, stiffness and disability were used as the primary efficacy measure, as well as the Laquesne index.

The WOMAC index stands for Western Ontario and McMaster Universities Osteoarthritis Index. This index is described in Double bind randomized control trial of sodium meclofenamate (Meclomen) and diclofenac sodium (Voltaren): post validation reapplication of the WOMAC Osteoarthritis Inde by Belany, N., Kean, W. F. Buchanan, W. W., Gerecz-Simon, E. and Campbell, J. *Jouraal of Rheumatology* 19:15–9;1992. The Lequesne index is described in Indices of severity and disease activity for osteoarthritis by Lequesne, M. *Seminars in Arthritis and Rheumatism*, 20:48–54;1991.

Study Methods

Visit 1. (Baseline)

Informed consent

Baseline assessments

Baseline bloods (FBE, E/LFT, ESR, CRP.)

Discontinue current treatment for osteoarthritis

Issue Paracetamol pack (60), with instructions that up to 8 per day in divided dose is acceptable.

Visit 2 (Injection)

The dipalmitoyl is warmed to body temperature and aspirated under sterile conditions into a syringe. Aseptic technique is used to deliver 2 mls of the substance into the knee, via medial approach.

Visit 2–8

Each visit:

Efficacy evaluation

Adverse reaction recording

Calculation of Paracetamol usage

New Paracetamol dispersed

Withdrawal

Patients were able to withdraw at anytime at the discretion of the investigator or at the wish of the patient.

Results

At the time of preparation of this patent application, the pilot human clinical trial was still ongoing, with 6 patients having completed the evaluation period, 3 patients under continuing evaluation and 1 patient who has withdrawn.

Only one patient out of the 10 treated developed an inflammatory reaction, which is less than predicted from experience with other intra-articular agents, and which cleared up in 2 days. Results to date are showing an unquestionable benefit, with specific features as follows:

1. All patients have demonstrated an improvement on almost all of their visits, the mean improvement for all visits up to 14 weeks is 49%, based on averaging the Womac and Lequesne scores.
2. All patients improve to a peak after which some slowly relapse towards their former state of disability, while others retain an appreciable (38–76%) improvement.
3. Patients reach peak anywhere from 2 to 10 weeks post-injection, averaging 4.8 weeks for the 6 patients who have completed the study.
4. Although the peaks are spread over several weeks for different patients the improvements they represent is 67–91%, averaging a 78% reduction in their disability.
5. Patients continue to show an improvement at 10 weeks of 47% and even 50% at 14 weeks, indicating an overall 50% improvement for bimonthly irrigations.
6. When questioned, all 6 of the patients who have completed the 15 week study claim they would opt for another injection if it were offered to them.

Full WOMAC pain, stiffness and disability and Lequesne index data is shown in Table 1 for each of patients II to IX. Note that patient I withdrew from the study and patients VI, IX and X are yet to complete the evaluation period. Percentage improvement over time post treatment is shown for patients II to X in FIG. 1. Percentage improvement is based on average WOMAC and Lequesne index scores.

TABLE 1

OSTEOARTHRITIC KNEES

| PATIENT | | | WOMAC | | | | | | LEQUESNE | |
|---|---|---|---|---|---|---|---|---|---|---|
| | | | Pain | | Stiffness | | Disability | | | |
| Age | Sex | | Test | Base | Test | Base | Test | Base | Mean Womac | Test | Base |

| | Age | Sex | Test | Base | Test | Base | Test | Base | Mean Womac | Test | Base |
|---|---|---|---|---|---|---|---|---|---|---|---|
| ONE WEEK POST-INJECTION (N = 9) | | | | | | | | | | | |
| ii | 60 | M | 1 | 10 | 1 | 0 | 6 | 16 | — | 5 | 13 |
| iii | 68 | M | 4 | 15 | 2 | 2 | 15 | 33 | — | 5 | 22 |
| iv | 71 | M | 6 | 8 | 3 | 5 | 23 | 31 | — | 14 | 17 |
| v | 61 | F | 5 | 12 | 0 | 6 | 2 | 39 | — | 3 | 19 |
| vi | 68 | M | 10 | 13 | 4 | 7 | 44 | 51 | — | 24 | 26 |
| vii | 60 | M | 6 | 10 | 4 | 4 | 32 | 33 | — | 13 | 21 |
| viii | 57 | M | 13 | 12 | 6 | 4 | 51 | 39 | — | 23 | 20 |
| ix | 56 | F | 5 | 10 | 2 | 2 | 17 | 20 | — | 12 | 12 |
| x | 72 | F | 10 | 14 | 3 | 6 | 36 | 60 | — | 27 | 30 |
| MEANS | | | 6.6 | 11.6 | 2.8 | 4.0 | 25.1 | 35.8 | — | 14.0 | 20.0 |
| IMPROVEMENT | | | 43% | — | 30% | — | 30% | — | 34% | 30% | — |
| TWO WEEKS POST-INJECTION (N = 9) | | | | | | | | | | | |
| ii | 60 | M | 1 | 10 | 0 | 0 | 6 | 16 | — | 6 | 13 |
| iii | 68 | M | 4 | 15 | 1 | 2 | 14 | 33 | — | 3 | 22 |
| iv | 71 | M | 12 | 8 | 5 | 5 | 31 | 31 | — | 16 | 17 |
| v | 61 | F | 0 | 12 | 1 | 6 | 2 | 39 | — | 3 | 19 |
| vi | 68 | M | 7 | 13 | 1 | 7 | 29 | 51 | — | 24 | 26 |
| vii | 60 | M | 4 | 10 | 1 | 4 | 7 | 33 | — | 6 | 21 |
| viii | 57 | M | 6 | 12 | 3 | 4 | 18 | 39 | — | 16 | 20 |
| ix | 56 | F | 5 | 10 | 2 | 2 | 17 | 20 | — | 12 | 12 |
| x | 72 | F | 9 | 14 | 3 | 6 | 40 | 60 | — | 27 | 30 |
| MEANS | | | 5.3 | 11.6 | 1.9 | 4.0 | 18.2 | 35.8 | — | 12.5 | 20.0 |
| IMPROVEMENT | | | 54% | — | 53% | — | 49% | — | 52% | 38% | — |

TABLE 1-continued

OSTEOARTHRITIC KNEES

| PATIENT | | | WOMAC | | | | | | LEQUESNE | |
|---|---|---|---|---|---|---|---|---|---|---|
| | | Pain | | Stiffness | | Disability | | Mean | | |
| Age | Sex | Test | Base | Test | Base | Test | Base | Womac | Test | Base |
| FOUR WEEKS POST-INJECTION (N = 9) | | | | | | | | | | |
| ii 60 | M | 1 | 10 | 0 | 0 | 0 | 16 | — | 2 | 13 |
| iii 68 | M | 3 | 15 | 2 | 2 | 15 | 33 | — | 7 | 22 |
| iv 71 | M | 6 | 8 | 3 | 5 | 14 | 31 | — | 9 | 17 |
| v 61 | F | 2 | 12 | 1 | 6 | 10 | 39 | — | 9 | 19 |
| vi 68 | M | 7 | 13 | 3 | 7 | 35 | 51 | — | 22 | 26 |
| vii 60 | M | 8 | 10 | 2 | 4 | 19 | 33 | — | 12 | 21 |
| viii 57 | M | 0 | 12 | 2 | 4 | 9 | 39 | — | 3 | 20 |
| ix 56 | F | 12 | 10 | 5 | 2 | 26 | 20 | — | 20 | 12 |
| x 72 | F | 12 | 14 | 4 | 6 | 48 | 60 | — | 26 | 30 |
| MEANS | | 5.6 | 11.6 | 2.4 | 4.0 | 19.3 | 35.8 | — | 12.2 | 20.0 |
| IMPROVEMENT | | 52% | — | 40% | — | 46% | — | 46% | 39% | — |
| SIX WEEKS POST-INJECTION (N = 8) | | | | | | | | | | |
| ii 60 | M | 5 | 10 | 2 | 0 | 18 | 16 | — | 10 | 13 |
| iii 68 | M | 7 | 15 | 4 | 2 | 21 | 33 | — | 8 | 22 |
| iv 71 | M | 6 | 8 | 4 | 5 | 15 | 31 | — | 9 | 17 |
| v 61 | F | 3 | 12 | 0 | 6 | 2 | 39 | — | 2 | 19 |
| vi 68 | M | 7 | 13 | 3 | 7 | 35 | 51 | — | 22 | 26 |
| vii 60 | M | 7 | 10 | 1 | 4 | 13 | 33 | — | 9 | 21 |
| viii 57 | M | 0 | 12 | 1 | 4 | 1 | 39 | — | 4 | 20 |
| ix 56 | F | 12 | 10 | 5 | 2 | 26 | 20 | — | 20 | 12 |
| MEANS | | 5.9 | 10.0 | 2.5 | 4.0 | 16.4 | 32.3 | — | 10.5 | 18.7 |
| IMPROVEMENT | | 41% | — | 38% | — | 49% | — | 43% | 44% | — |
| TEN WEEKS POST-INJECTION (N = 7) | | | | | | | | | | |
| ii 60 | M | 7 | 10 | 0 | 0 | 12 | 16 | — | 14 | 13 |
| iii 68 | M | 10 | 15 | 6 | 2 | 36 | 33 | — | 16 | 22 |
| iv 71 | M | 4 | 8 | 1 | 5 | 6 | 31 | — | 7 | 17 |
| v 61 | F | 9 | 12 | 2 | 6 | 30 | 39 | — | 16 | 19 |
| vii 60 | M | 5 | 10 | 1 | 4 | 8 | 33 | — | 9 | 21 |
| viii 57 | M | 0 | 12 | 1 | 4 | 3 | 39 | — | 5 | 20 |
| ix 56 | F | 10 | 10 | 3 | 2 | 26 | 20 | — | 22 | 12 |
| MEANS | | 6.4 | 12.4 | 2.0 | 3.3 | 17.3 | 30.1 | — | 12.7 | 17.7 |
| IMPROVEMENT | | 48% | — | 39% | — | 43% | — | 43% | 28% | — |
| FOURTEEN WEEKS POST-INJECTION (N = 6) | | | | | | | | | | |
| ii 60 | M | 3 | 10 | 1 | 0 | 6 | 16 | — | 8 | 13 |
| iii 68 | M | 10 | 15 | 5 | 2 | 38 | 33 | — | 18 | 22 |
| iv 71 | M | 5 | 8 | 1 | 5 | 8 | 31 | — | 6 | 17 |
| v 61 | F | 11 | 12 | 4 | 6 | 35 | 39 | — | 18 | 19 |
| vii 60 | M | 3 | 10 | 1 | 4 | 11 | 33 | — | 10 | 21 |
| viii 57 | M | 1 | 12 | 1 | 4 | 5 | 39 | — | 7 | 20 |
| MEANS | | 5.5 | 11.2 | 2.1 | 3.5 | 17.2 | 31.8 | — | 11.2 | 17.0 |
| IMPROVEMENT | | 51% | — | 40% | — | 46% | — | 46% | 34% | — |

Example 3

Lubrication of surgical instruments

For a hip or knee replacement to be successful the prosthetic knee or hip needs to be firmly secured to the shaft of a healthy living bone, giving it a secure mechanical base that can withstand the body's load. In the surgical procedure the hip or knee to be replaced must be sawn off using a bone saw. However, use of the saw generates heat and, in some cases, this reaches the state where smoke is being emitted from the cut. In some patients the arthritic joint is particularly difficult to cut and heating is exacerbated if the the arthritic joint is particularly difficult to cut and heating is exacerbated if the saw blades are at all blunt.

A long-term problem arises when the heat generated in the bone by the saw kills osteocytes and other bone cells, such that the new hip or knee is no longer attached to healthy living bone. After weeks or months this dead bone disintegrates, compromising the mechanical base securing the implant, often with disastrous results for the patient.

A very few simple experiments have been carried out:

1. When cutting a normal bovine bone with a hacksaw, little heat was generated. However the saw blade was very soon coated with a hydrophobic coating, elevating the contact angle of a droplet of saline from 0 to 35°–67°. Upon rinsing the blade with a lipid solvent the lipid coating was found to contain an appreciable quantity of SAPL. It is therefore likely that, in sawing off arthritic joints known to be deficient in SAPL, there will be less SAPL naturally available to lubricate the blade—hence the excessive heat generated.

2. When using the same hacksaw to cut a block of wood it was found that the unlubricated blade became quite hot as monitored by an infra-red thermometer. Upon lubricating the blade with inventive composition, the temperature was appreciably reduced.

The composition can be applied to the saw blade in three forms:

(i) a solution of DPPC in propylene glycol (ii) a solution of DPPC in ethanol where the ethanol can evaporate leaving the DPPC as a thin layer of 'wax' on the surface. This mode would be ideal for sterilizing the pre-lubricated saw blade by autoctaving.

(iii) a suspension of DPPC and/or other phospholipids as a fluid for irrigating the saw cut as soon as heat starts to be generated in the bone. We would suggest monitoring the bone-saw blade with an infra-red thermometer which is a non-invasive technique.

Ancillary Applications

1. The product can be used to lubricate a scalpel or any knife edge cutting tissue, e.g. as a lubricant on a microtome.
2. it can also be used to reduce the force needed to penetrate skin or other tissue with a needle, e.g. a hypodermic needle where the force to penetrate rubber is reduced by 57%.
3. Lubricating bone saws to reduce the heat which kills osteocytes (bone-cells) and thus compromises implantation of prosthetic hips, etc.
4. Lubricating artificial hips and knees upon implantation.
5. Lubricating various indwelling devices such as catheters, pacemakers, etc. to reduce wear of the adjacent tissue.
6. Our studies have shown that SAPL tends to prevent surgical adhesions which can be a major problem in surgery, including laparoscopy.

What is claimed is:

1. A method of lubricating a mammalian joint or other physiological articulation which comprises administering to said joint or said articulation in need of such treatment an effective amount of a composition comprising one or more phospholipids in association with propylene glycol.

2. The method according to claim 1 wherein administration of said composition is to a joint affected by arthritis.

3. The method according to claim 1 wherein administration of said composition is to a prosthetic or partly prosthetic joint.

4. The method according to claim 1 wherein administration of said composition is during or after surgery on said joint or physiological articulation.

5. The method according to claim 4 wherein said surgery is to implant a prosthetic or partly prosthetic joint.

6. The method according to claim 1 wherein said composition comprises between about 25 mg to about 500 mg phospholipid per 1 ml propylene glycol.

7. The method according to claim 6 wherein said composition comprises between about 50 mg to about 300 mg phospholipid per 1 ml propylene glycol.

8. The method according to claim 6 wherein said composition comprises about 200 mg phospholipid per 1 ml propylene glycol.

9. The method according to claim 1 wherein said composition is administered in a volume of between about 0.1 ml to about 10 ml.

10. The method according to claim 9 wherein said composition is administered in a volume of between about 0.5 ml to about 5 ml.

11. The method according to claim 10 wherein said composition is administered in a volume of about 2 ml.

12. The method according to claim 1 wherein administration of said composition is by direct injection to the joint or other physiological articulation.

13. The method according to claim 1 wherein said one or more phospholipids are selected from the group consisting of sphingolipids and phosphoglycerides.

14. The method according to claim 13 wherein said one or more phospholipids are selected from the group consisting of phosphatidylcholine, phosphatidylethanolamine, phosphatidylserine, phosphatidylglycerol, phosphatidylinositol, sphingomyelin and derivatives thereof which are suitable in lubricant compositions.

15. The method according to claim 14 wherein said phospholipid is alpha-dipalmitoyl phosphatidylcholine.

16. The method according to claim 1 wherein said mammal is a human.

17. The method according to claim 15 wherein said phospholipid is racemic alpha-dipalmitoyl phosphatidylcholine.

18. The method according to claim 15 wherein said phospholipid is L-enantiomeric alpha-dipalmitoyl phosphatidylcholine.

* * * * *